(12) United States Patent
Yokoyama et al.

(10) Patent No.: US 6,198,796 B1
(45) Date of Patent: Mar. 6, 2001

(54) METHOD AND APPARATUS OF AUTOMATICALLY SELECTING BRAGG REFLECTIONS, METHOD AND SYSTEM OF AUTOMATICALLY DETERMINING CRYSTALLOGRAPHIC ORIENTATION

(75) Inventors: Ryoichi Yokoyama; Jimpei Harada, both of Tokyo (JP)

(73) Assignee: Rigaku Corporation, Tokyo (JP)

(*) Notice: Subject to any disclaimer, the term of this patent is extended or adjusted under 35 U.S.C. 154(b) by 0 days.

(21) Appl. No.: 09/321,554

(22) Filed: May 28, 1999

(30) Foreign Application Priority Data

Jun. 2, 1998 (JP) .................................. 10-153422
May 26, 1999 (JP) .................................. 11-146379

(51) Int. Cl.$^7$ .................................................. G01N 23/20
(52) U.S. Cl. .................................. 378/73; 378/76; 378/81
(58) Field of Search .............................. 378/73, 76, 81

(56) References Cited

U.S. PATENT DOCUMENTS 4,119,498 * 10/1978 Edwall et al. ................. 205/782
4,412,345 * 10/1983 Workman et al. ............... 378/78

FOREIGN PATENT DOCUMENTS

000962762A2 * 8/1999 (EP) .

* cited by examiner

Primary Examiner—David V. Bruce
(74) Attorney, Agent, or Firm—Wenderoth, Lind & Ponack, L.L.P.

(57) ABSTRACT

A novel method and novel apparatus that are capable of selecting, with a computer, reference Bragg reflections pc1 and pc2, which form a basis for determination of the crystallographic orientation of a crystal sample by the two-reflection method, automatically and easily and accurately, wherein; firstly, x-ray intensities and diffraction conditions of all Bragg reflections which are measurable are calculated using the crystallographic information, secondly, a weight-point according to both the x-ray intensity and the angle between the sample normal and the scattering vector is obtained for each of the Bragg reflections, thirdly, two Bragg reflections having the two largest weight-points are selected as the reference Bragg reflections pc1 and pc2, respectively.

29 Claims, 9 Drawing Sheets

METHOD AND APPARATUS OF AUTOMATICALLY SELECTING BRAGG REFLECTIONS, METHOD AND SYSTEM OF AUTOMATICALLY DETERMINING CRYSTALLOGRAPHIC ORIENTATION

BACKGROUND OF THE INVENTION

1. Field of the Invention

The present invention relates to a method and apparatus for automatically selecting Bragg reflections and to a method and system for automatically determining crystallographic orientation, which are useful in analyzing and characterizing structures of crystal samples such as wafers for semiconductor and thin films deposited on the wafers.

2. Description of the Related Art

In crystal structure analysis developed for analysis of atomic structure, x-rays, or particles beams such as neutron beams or electron beams are applied to a crystal sample with the unknown structure, and then, using diffraction phenomenon of rays scattered by the crystal sample, the lattice type of the crystal sample or the atomic arrangement in the lattice are clarified. In this crystal structure analysis, for example, x-rays are used for the analysis of electron density in the crystal sample, neutron beams are used for the analysis of atomic nuclei positions in the crystal sample, and electron beams are used for the analysis of electric potential in the crystal sample.

On the other hand, a method, so-called two-reflection method, for determining the crystallographic orientation of a crystal sample having known crystal structure has been utilized frequently. In this two-reflection method, two Bragg reflections in the recipricol space of the crystal sample are searched, and then the crystallographic orientation are determined using the positions of the obtained two Bragg reflections.

More specifically, in this two-reflection method, first, when the reciprocal lattice of a crystal sample is at the standard position, reference Bragg reflections $K_1$ and $K_2$ together forming a basis for determination of crystallographic orientation of this crystal sample are selected arbitrarily, as shown in FIG. 1($a$). Next, actual Bragg reflections $K_1'$ and $K_2'$ satisfying their diffraction conditions, i.e., 2θ-angles, ω-angles, χ-angles, and φ-angles, of the reference Bragg reflections $K_1$ and $K_2$, respectively, are actually measured with a four-axis goniometer system, as shown in FIG. 1($b$). Then, rotation angle from the reference position of the reciprocal lattice is determined using the positions of the actual Bragg reflections $K_1'$ and $K_2'$ (i.e., using the rotation angles from the reference Bragg reflections $K_1$ and $K_2$ to the actual Bragg reflections $K_1'$ and $K_2'$). In this way, the actual crystallographic orientation of the crystal sample are determined.

A four-axis goniometer system is well-known in the art. For example, as shown in FIGS. 2 and 3, the four-axis goniometer system comprises a 4-axis goniometer 100 having four rotating axes (i.e., an Ω-axis for determining the crystal direction of a crystal sample 200, a X-Φ assembly carried on the Ω-axis, and 2θ-axis for detecting diffracted x-rays), an x-ray source 110, a detector 120 such as an x-ray counter for detecting diffracted rays, a computer 130 used for control, and a 2θ-rotation driving device 141, an Ω-rotation driving device 142, a χ-rotation driving device 143 and a φ-rotation driving device 144 for rotating the respective rotation axes of the 4-axis goniometer 100. The computer 130 has a CPU 131, a memory 132, and a CRT display 133.

The rotation angles of the 2θ-axis, Ω-axis, X-axis, and the φ-axis of the 4-axis goniometer 100 are, respectively, 2Φ-angle that is the angle of diffraction, ω-angle that is the angle of incidence, χ-angle that is the tilt angle of the crystal sample 200, and φ-angle that is the angular position of the crystal sample 200 on the Φ-axis.

The computer 130 controls the 2θ-rotation driving device 141, the ω-rotation driving device 142, the χ-rotation driving device 143, and the φ-rotation driving device 144 so as to rotate the 2θ-axis, Ω-axis, X-axis, and Φ-axis so that the actual angles of the 4-axis goniometer 100 becomes equal to the diffraction conditions, i.e., 2θ-angles, ω-angles, χ-angles, and φ-angles, of the reference Bragg reflections $K_1$ and $K_2$. Then, the diffracted x-rays at these 2θ-angles, ω-angles, χ-angles, and φ-angles, i.e., the actual Bragg Reflections $K_1'$ and $K_2'$ satisfying the diffraction conditions, are detected by the detector 120.

However, in this prior art method for determining the crystallographic orientation using the two-reflection method described above, the two reference Bragg reflections $K_1$ and $K_2$ forming a basis for the determination of the crystallographic orientation must be selected manually. Automatic selection techniques using a computer are not yet established. Therefore, after selecting the reference Bragg reflections $K_1$ and $K_2$ manually, actual Bragg reflections $K_1'$ and $K_2'$ must be measured in additional experiments to find the positions accurately, and then the crystallographic orientation are computed. Thus, determination of the crystallographic orientation in one continuous process could not have been made, thereby making it very cumbersome to perform and time-consuming. Consequently, there has been a great demand for an technique capable of automatically determining the crystallographic orientation in one continuous process.

SUMMARY OF THE INVENTION

The present invention has been made in view of the foregoing circumstances, and it is an object of the present invention to provide a novel method and apparatus that are free of the foregoing problems with the prior art technique and are capable of selecting Bragg reflections automatically and easily.

this method and apparatus automatically select two Bragg reflections as reference Bragg reflections pc1 and pc2, using a computer. The reference Bragg reflections pc1 and pc2 form a basis for determination of crystallographic orientation of a crystal sample by the two-reflection method. First, x-ray intensities and diffraction conditions of all Bragg reflections which are measurable are calculated using crystallographic information given to the computer. This crystallographic information is information intrinsic to crystals of the crystal sample, such as space groups, lattice constants and atomic positions, and the diffraction conditions to be calculated using such crystallographic information are 2θ-angles, ω-angles, χ-angles, and φ-angles. Next, a weight-point is obtained and assigned to each of the Bragg reflections according to both its x-ray intensity and its angle (hereinafter denoted by ΔG) between the sample normal and its scattering vector. Then, two Bragg reflections having the first and second largest weight-points are selected as the reference Bragg reflections pc1 and pc2.

It is another object of the invention to provide a novel method and apparatus that are free of the foregoing problems with the prior art technique and are capable of automatically selecting Bragg reflections and of determining the crystallographic orientation of a crystal sample automatically and easily.

This method and system use a computer for performing various calculations and a four-axis goniometer system for performing various measurements according to the results of calculations made by the computer. First, x-ray intensities and diffraction conditions, i.e., 2θ-angles, ω-angles, χ-angles, and φ-angles, of all Bragg reflections which are measurable are calculated using crystallographic information such as space groups, lattice constants and atomic positions. Next, a weight-point is obtained and assigned to each of the Bragg reflections according to both its x-ray intensity and its angle ΔG between the sample normal and its scattering vector, and the two Bragg reflections having the first and second largest weights are selected as the reference Bragg reflections pc1 and pc2, respectively. Thereafter, the four-axis goniometer system searches and measures actual Bragg reflections pc1 and pc2 actually satisfying the same diffraction conditions of the reference Bragg reflections pc1 and pc2, respectively. Then, the angle $\alpha_0$ between the actual Bragg reflections po1 and po2 is calculated. And, equivalent reflections of each of the reference Bragg reflections pc1 and pc2 are found by symmetrical operations. These equivalent reflections are searched for a combination of equivalent reflections pc1' and pc2' where the angle therebetween equals to the angle $\alpha_0$ and also the crystal axes thereof coincide, respectively, with those of the reference Bragg reflections pc1 and pc2. Finally, the crystallographic orientation is obtained from these equivalent reflections pc1' and pc2' by the two-reflection method.

BRIEF DESCRIPTION OF THE DRAWINGS

The foregoing and other objects, features and advantages of the present invention will be apparent from the following more particular description of preferred embodiments of the invention, taken in conjunction with the accompanying drawings, in which.

DETAILED DESCRIPTION OF THE INVENTION

Figure 4:
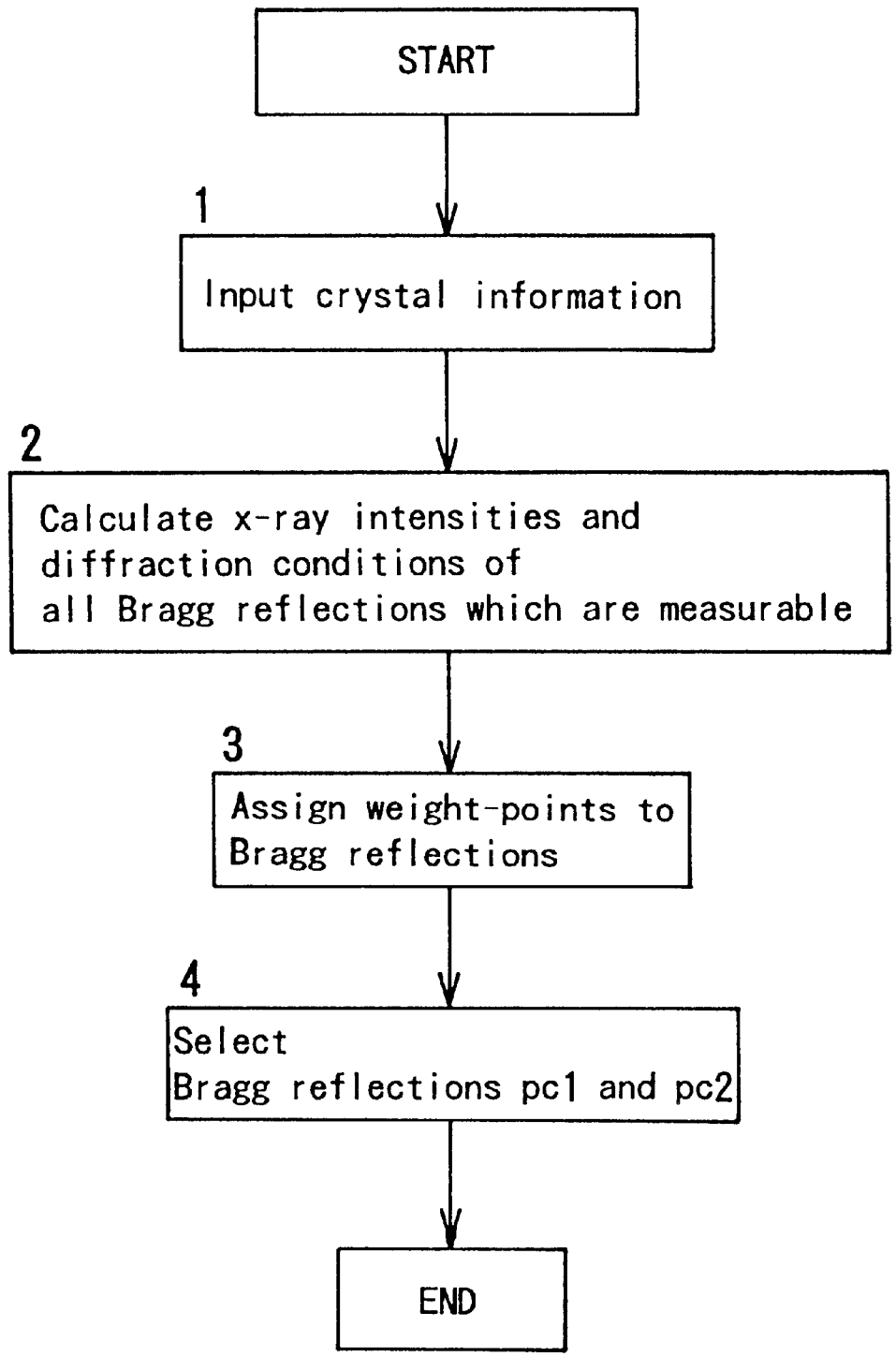
FIG. 4 is a flowchart illustrating process steps of a method of automatically selecting Bragg reflections in accordance with the present invention.

FIG. 4 is a flowchart illustrating the process steps of a method for automatically selecting Bragg reflections in accordance with the present invention. This method uses a computer to automatically select two Bragg reflection as reference Bragg reflections pc1 pc 2 which together form a basis for determination of the crystallographic orientation of a crystal sample by the aforementioned well-known two-reflection method.

Referring to FIG. 4, firstly, crystallographic information is entered into the computer [step 1]. The crystallographic information includes, for example, space groups, lattice constants, atomic positions, temperature constants, sample normals, and the direction of the incident x-rays.

Secondly, x-ray intensities and diffraction conditions, i.e., 2θ-angles, ω-angles, χ-angles, and φ-angles, of all Bragg reflections which are measurable are calculated using the entered crystallographic information [step 2]. Each x-ray intensity is substantially equal to the square of the structure factor of a Bragg reflection calculated by a well-known method using a space group, lattice constants, atomic positions, and temperature constants. With respect to the diffraction conditions, for example, if any one of the incident angle, the reflection outgoing angle, the ω-angle, the χ-angle, and the φ-angle is constant, the ω-angle, χ-angle, and φ-angle are computed while keeping 2θ constant.

Thirdly, a weight-point is assigned to each of the Bragg reflections according to its x-ray intensity and its angle ΔG between the sample normal and its scattering vector [step 3].

In this step 3 for assigning weight-points, first, a point A for each of the Bragg reflections is obtained by normalizing its structure factor with the structure factor of the Bragg reflection having the maximum x-ray intensity, that is the maximum magnitude of the structure factor which is regarded as the intensity [step 31]. In other words, a value of the point A represents the structure factor of each of the Bragg reflections normalized with the structure factor of the Bragg reflection having the maximum x-ray intensity. Thus, for example, the value of normalized structure factor of the Bragg reflection having the maximum x-ray intensity is 1.0, which is the point A for the Bragg reflection having the maximum x-ray intensity. Consequently, the Bragg reflections with larger x-ray intensities have higher values of the points A.

Also, a point B for each of the Bragg reflections is obtained by calculating the cosine of its angle ΔG [step 31]. In other words, the value of the point B represents the cosine of the angle ΔG for each of the Bragg reflections. Thus, for example, the cosine of the angle ΔG=0° is 1, which is the point B for the Bragg reflection having the angle ΔG=0°, and the cosine of the angle ΔG=90° is 0, which is the point B for the Bragg reflection having the angle ΔG=90°. Consequently, the Bragg reflections with the angle ΔG closer to 0° have higher values of points B.

Further, the values m and n which represent the occupancies (or the dominance) of the point A and the point B in the weight-points are entered into the computer [step 32]. These m and n are for deciding which point A or B is more dominant or less dominant in obtaining the weight-point as below. The values of m and n are chosen arbitrarily depending on the results of experiment (or experimental knowledge) previously done about crystal of various crystal samples. Thus, these values of m and n may vary depending on crystal samples. For example, m:n=7:3 may be preferable for any crystal in terms of experimental results, meaning point A is considered more dominate that point B in obtaining weight-points. Further, for example, after choosing the value of m, the value of n may be calculated by subtracting the value of m from 100.

Then, with respect to the each of the Bragg reflections, using its point A and point B obtained as described above and the values m and n entered as described above, each weight-point for each of the Bragg reflections is calculated by the equation A×m/100+B×n/100 [step 33].

Fourthly, after this assigning process of weight-points, one Bragg reflection having the largest weight-point and another Bragg reflection having the second largest weight-point are selected as reference Bragg reflections pc1 and pc2, respectively, from all the Bragg reflections to which the weight-points have been assigned as described above [step 4]. However, if the second Bragg reflection is on the line drawn by the origin and the first Bragg reflection, the next Bragg reflection not on the line (e.g., the third Bragg reflection) is selected. That is, it is required that the two Bragg reflections selected as the reference Bragg reflections pc1 and pc2 be not on the line.

The processing described thus far is conducted by the computer. Therefore, the two reference Bragg reflections pc1 and pc2 together forming a basis in determination of the crystallographic orientation can be selected easily and automatically by simply entering required data into the computer.

Figure 1A:
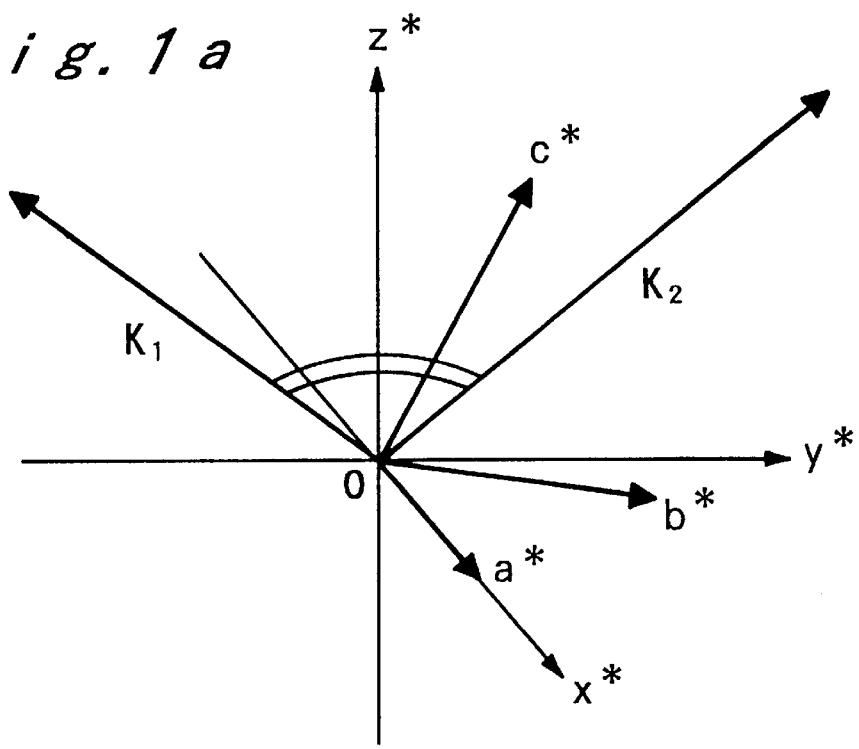
FIGS. 1(a) and 1(b) are a schematic diagram illustrating a method of determining a crystallographic orientation by the two-reflection method.
Figure 1B:
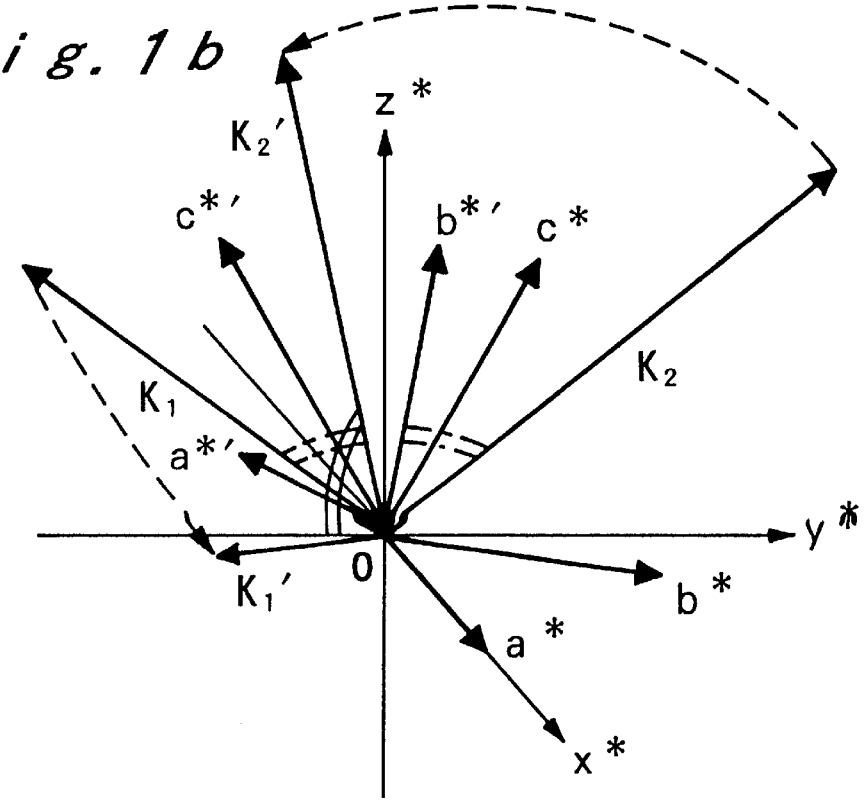
Figure 2:
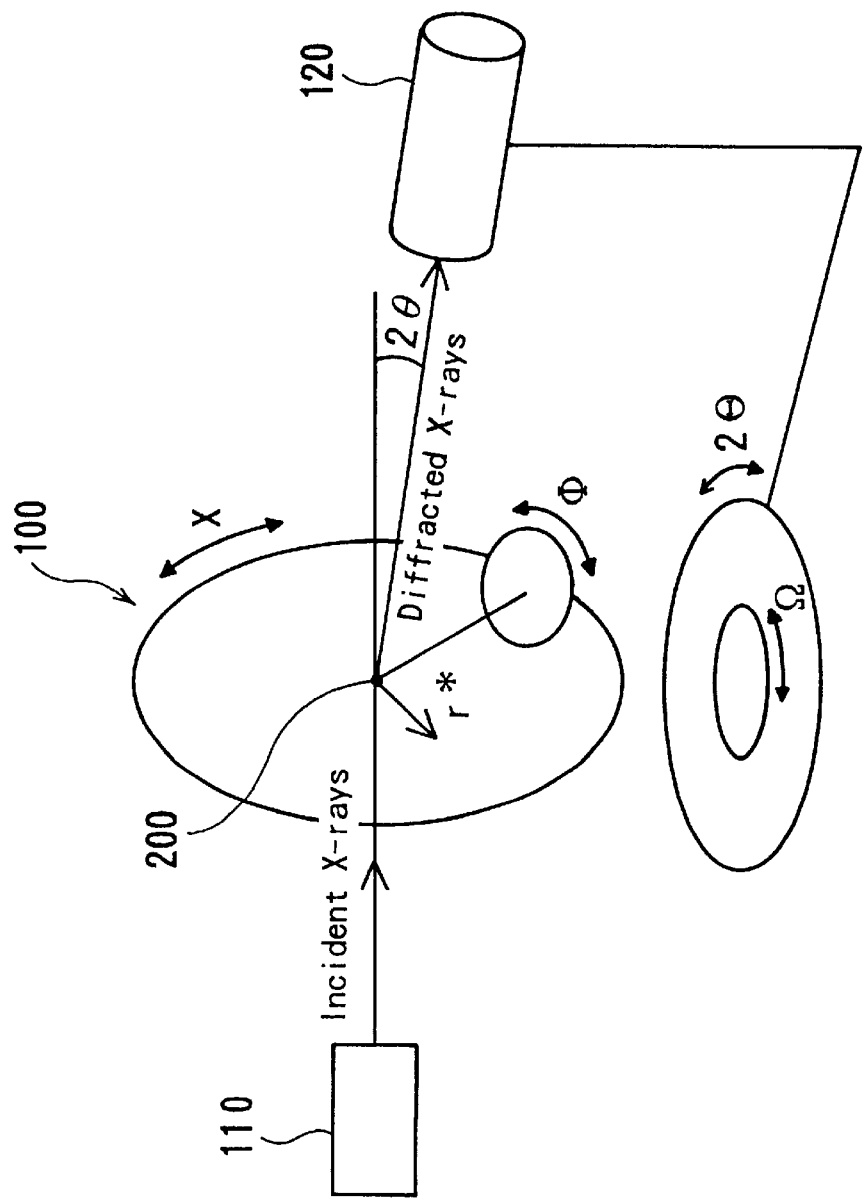
FIG. 2 is a schematic diagram illustrating the rotation axes of a 4-axis goniometer in a well-known four-axis goniometer system.
Figure 3:
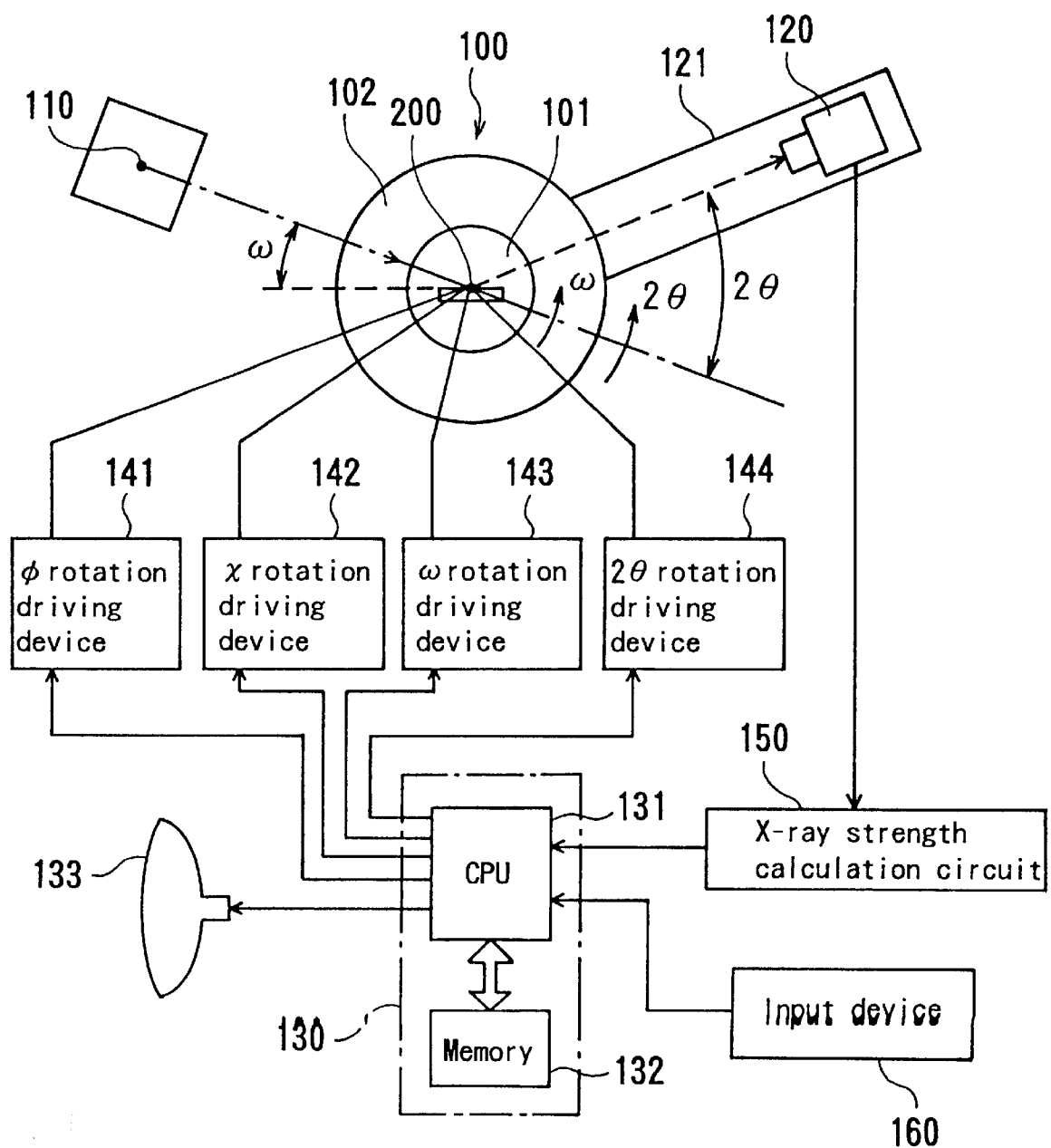
FIG. 3 is a schematic block diagram of main portions of the well-known four-axis goniometer system shown in FIG. 2.

Then, by using the well-known four-axis goniometer system as shown in FIGS. 2 and 3, two actual Bragg reflections which actually satisfy the diffraction conditions of the reference Bragg reflections pc1 and pc2, respectively, are searched and measured, and the orientation of the reciprocal lattice is found using the rotation angles of the actual Bragg reflections from the respective reference Bragg reflections, thereby determining the crystallographic orientation of the crystal sample.

Since the selection of the two reference Bragg reflections is automated using a computer in accordance with the automatic Bragg reflection selection method of the present invention as described above, the selections, measurements, and calculations can be performed in one process automatically by the use of the computer 130 of the four-axis goniometer system such as the one shown in FIGS. 2 and 3. Hence, quick and easy determination of the crystallographic orientation can be realized.

Of course, the two reference Bragg reflections may be selected by the method according to the present invention through a computer separate from the computer 130 of the four-axis goniometer system. In this case, data is transmitted between the two computers, thereby the crystallographic orientation can be determined automatically in one continuous operation.

Figure 5:
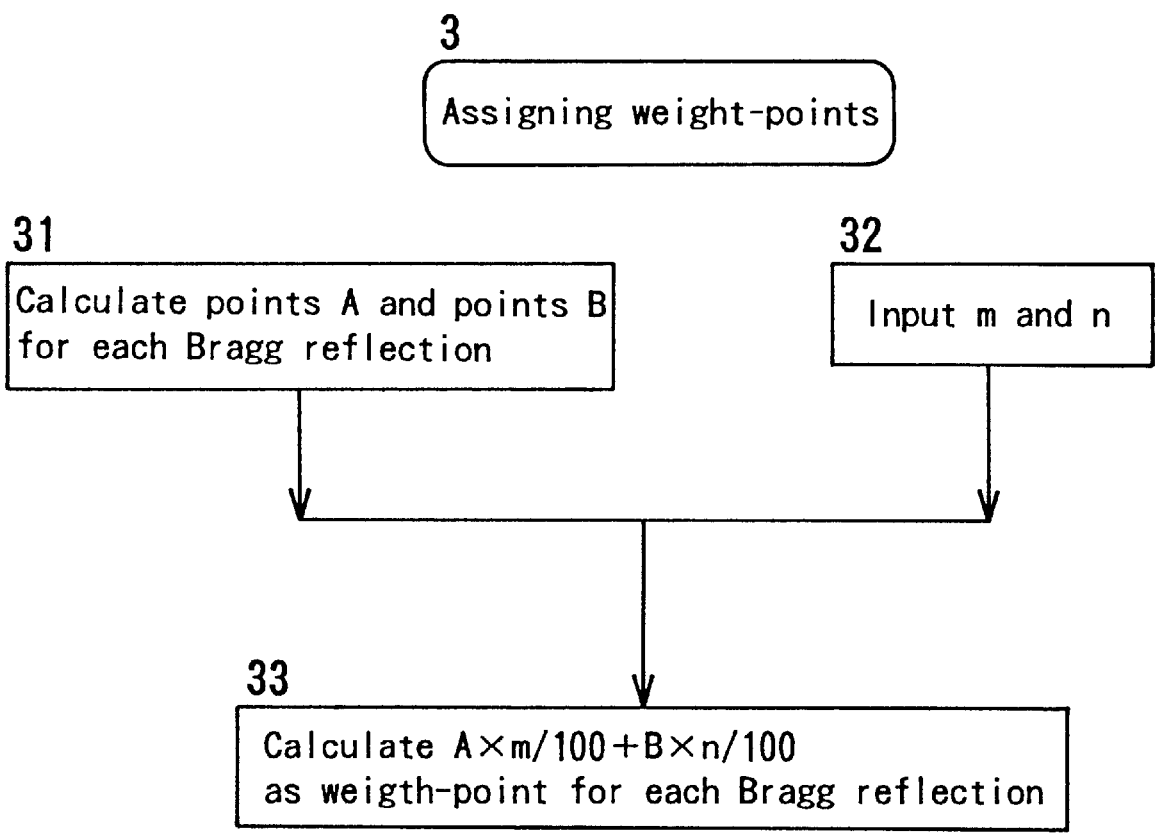
FIG. 5 is a flowchart illustrating process steps of weighting processing.
Figure 6:
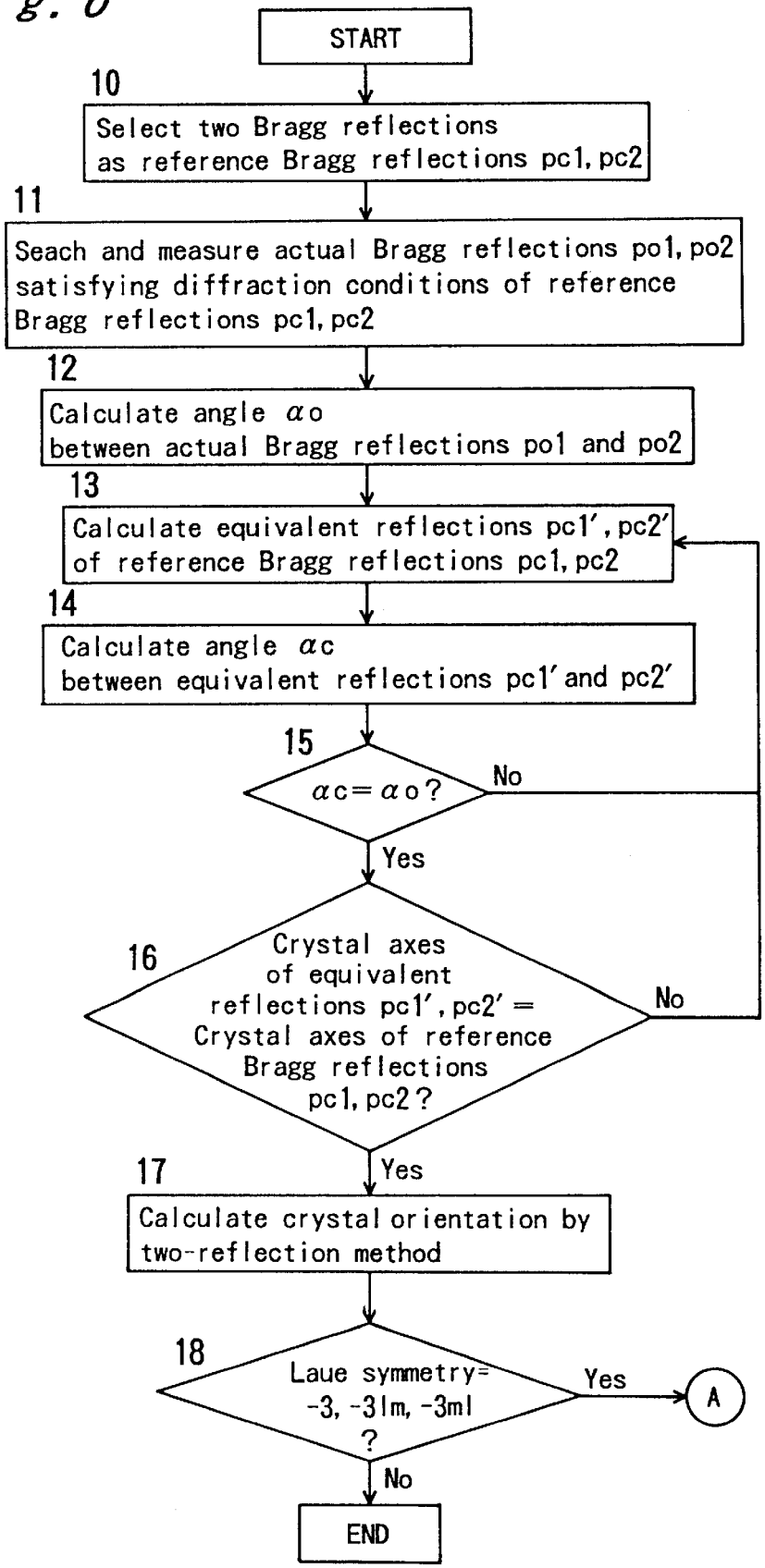
FIG. 6 is a flowchart illustrating a method of automatically determining crystallographic orientation in accordance with the present invention.

FIG. 6 is a flow chart illustrating the processing by an automatic crystallographic orientation determination method in accordance with the present invention. As illustrated in FIG. 6, in this method of automatically determining the crystallographic orientation in accordance with the present invention, the computer selects the two reference Bragg reflections pc1 and pc2 together forming a basis for determination of the crystallographic orientation in the same way as the processing already described in connection with FIGS. 4 and 5. That is, automatic selection is done through the calculation process of the x-ray intensities and diffraction conditions, the weight-points assigning process, and the selection process as described above [step 10].

Then, the diffraction conditions of the reference Bragg reflections pc1 and pc2 are sent to the four-axis goniometer system. This four-axis goniometer system searches and measures actual Bragg reflections po1 and po2, each satisfying the diffraction conditions of the reference Bragg reflections pc1 and pc2, respectively [step 11]. The well-known four-axis goniometer system such as the one exemplified in FIGS. 2 and 3 is used.

Hereupon, if the actual Bragg reflections po1 and po2 are their equivalent reflections, there arises the possibility that misidentifying of the true crystal structure might be occurred. Therefore, in the method in accordance with the present invention, the following process is performed to find the correct crystallographic orientation and to analyze the true crystal structure.

First, the computer calculates an angle $\alpha_0$ between the scattering vectors of the actual Bragg reflections po1 and po2 [step 12].

Then, equivalent reflections for each of the reference Bragg reflections pc1 and pc2 are obtained by symmetrical operations, and a combination of equivalent reflections pc1' and pc2' is selected from the obtained equivalent reflections, wherein the combination has the angle between the equivalent reflections pc1' and pc2' equal to the angle $\alpha_0$ and also has the scattering vector length of the equivalent reflection pc1' coincident with that of the reference Bragg reflect pc1 and the scattering vector length of the equivalent reflection pc2' coincident with that of the reference Bragg reflection pc2.

More particularly, the equivalent reflection pc1' of the reference Bragg reflection pc1 and the equivalent reflection pc2' of the reference Bragg reflection pc2 are obtained by symmetrical operations [step 13]. The angle $\alpha_c$ between the equivalent reflections pc1' and pc2' is calculated [step 14].

Then, a decision is made as to whether this angle $\alpha_c$ is equal to the angle $\alpha_0$ between the Bragg reflections po1 and po2 [step 15].

If they do not agree, other equivalent reflections pc1' and pc2' are obtained again by symmetrical operations, and the angle $\alpha_c$ between them is computed, and again a decision is made as to whether this angle $\alpha_c$ is equal to the angle $\alpha_0$. This sequence of steps 13–15 is carried out until equivalent reflections pc1' and pc2' with $\alpha_c = \alpha_0$ are obtained.

If equivalent reflections pc1' and pc2' having $\alpha_c$ equal to $\alpha_0$ are obtained, a next decision is then made as to whether the scattering vector lengths of the equivalent reflections pc1' and pc2' are coincident with the scattering vector lengths of the reference Bragg reflections pc1 and pc2, respectively [step 16]. If they do not agree, other equivalent reflections pc1' and pc2' having $\alpha_c$ equal to $\alpha_0$ are again found as described above [steps 13–15], and again a decision is made as to whether the scattering vector lengths are coincident with each other [step 16]. This series of step 13–16 is carried out until equivalent reflections pc1' and pc2' with coincident lengths are obtained.

Finally, with respect to the equivalent reflections pc1' and pc2' selected in this way, the crystallographic orientation is calculated by the well-known two-reflection method as mentioned previously [step 17]. For example, in the four-axis goniometer system exemplified in FIG. 3, the 4-axis goniometer 100 searches and measures two actual Bragg reflections po1 and po2 satisfying the diffraction conditions of the equivalent reflections pc1' and pc2', respectively. The computer 130 finds the orientation of the reciprocal lattice, using the rotation angle from the equivalent reflections pc1' and pc2' to the actual Bragg reflections po1 and po2, respectively. Finally, the crystallographic orientation of the crystal sample is determined. The off angle between the sample normal and a specified surface normal, and the angle between the direction of the incident x-rays and a specified input direction are computed as the crystallographic orientation, for example.

Since the above-described processing steps are carried out by the computer and the four-axis goniometer system, the crystallographic orientation are automatically determined and the crystal structure of the crystal sample can be analyzed simply by entering requisite data such as a crystallographic information into the computer.

In the case where a crystal system of the crystal structure having the crystallographic orientation determined through the processing steps 10–17 is trigonal, if the Laue symmetry indicating the symmetry in the reciprocal space of the crystal is given by any one of –3, –31 m, and –3 ml, then the crystal structure might be shifted by 60 ° (in the positive or negative direction) along the c-axis with respect to the true structure.

Accordingly, in the automatic crystallographic orientation determining method of the present invention, a Bragg reflection p1 and another Bragg reflection p2 obtained by shifting the Bragg reflection p1 by 60° along the c-axis are selected from the crystal structure if the crystal system of the analyzed crystal structure is trigonal, that is if the Laue symmetry (=Laue group) is given by any one of –3, –31 m, and –3 ml [step 18 Yes]. And, the x-ray intensity of the Bragg reflection p1 is compared with the x-ray intensity of the Bragg reflection p2. Then, a decision is made if the relation in magnitude between the x-ray intensities of the Bragg reflection p1 and the Bragg reflection p2 agrees with the relation in magnitude between the structure factors of the Bragg reflection p1 and the Bragg reflection p2. If they do not agree, the crystal structure is shifted by 60°, thus obtaining the true crystal structure.

Figure 7:
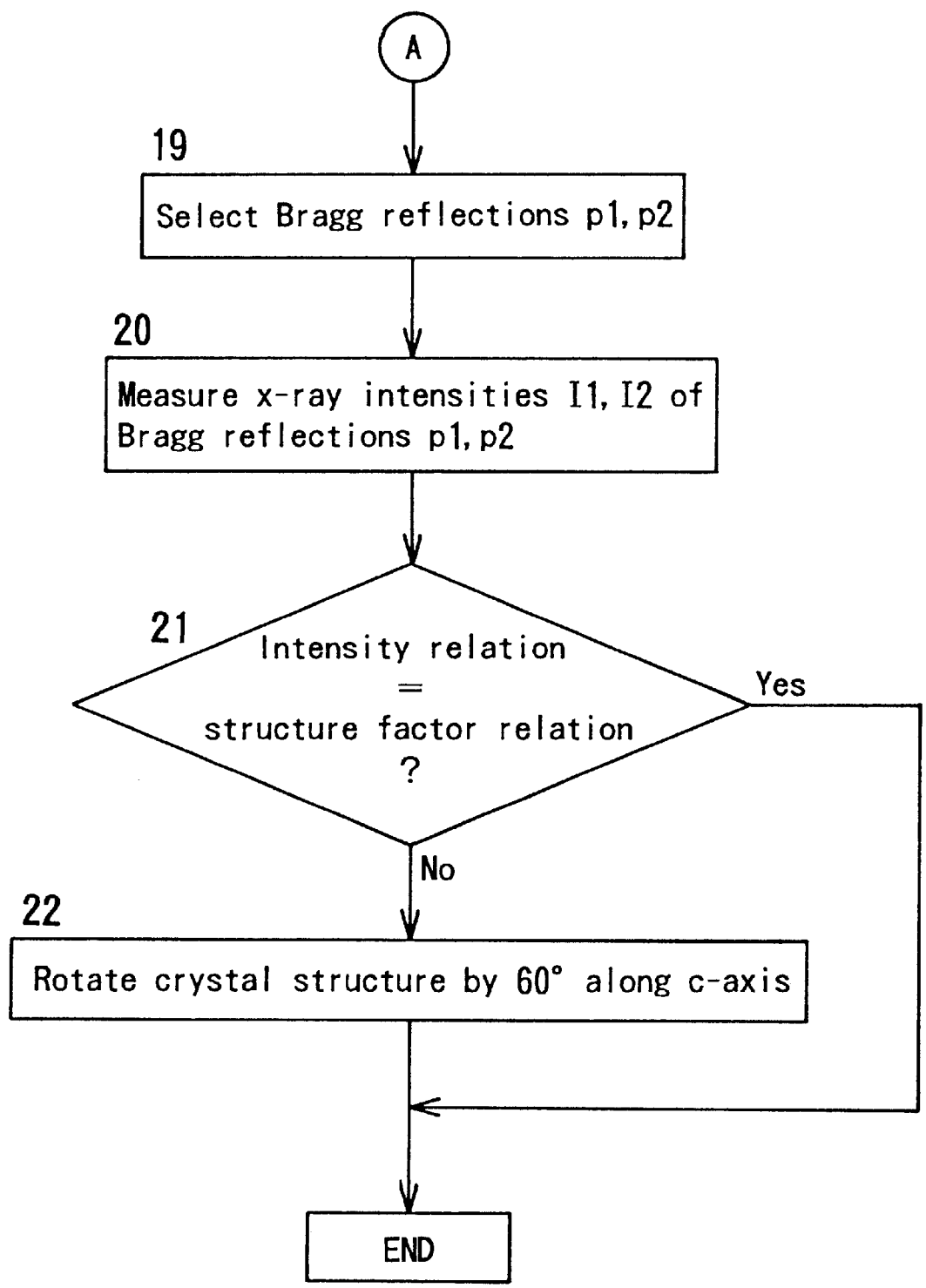
FIG. 7 is a flowchart illustrating processing for rotation axes where the crystal is a trigonal system.

More particularly, this processing is conducted as illustrated in FIG. 7. First, a Bragg reflection p1 which is not on the c-axis and a Bragg reflection p2 which is not on the c-axis and obtained by rotating the Bragg reflection p1 by 60° along the c-axis are selected [step 19]. The diffraction conditions are sent to the four-axis goniometer system. It is preferable that the Bragg reflections p1 and p2 differ widely in magnitude.

Then, the four-axis goniometer system measures the x-ray intensities I1 and I2 of the Bragg reflections p1 and p2, respectively [step 20].

The x-ray intensities I1 and I2 measured by the four-axis goniometer system are sent to the computer, which then makes a decision as to whether the relation in magnitude between the x-ray intensities I1 and I2 is coincident with the relation in magnitude between the structure factors of the Bragg reflections p1 and p2 [step 21]. If they do not agree, the original crystal structure is rotated by 60° along the c-axis [step 22].

Consequently, although it has been impossible in the past to determine the crystallographic orientation of a crystal sample having a trigonal system by the prior art two-reflection method, in accordance with the present invention, such determination can be achieved very easily by the use of a computer, and thus the crystal structure can be analyzed precisely.

In addition, to make the above-calculated crystallographic orientation as close as possible to or as same as the crystallographic orientation separately calculated from the crystallographic information, an axis conversion of the crystal, i.e., a conversion where axes are replaced without varying the crystal structure, may be done. The crystallographic orientation can be found with higher accuracy by performing such crystal axis conversion automatically by computer.

Figure 8:
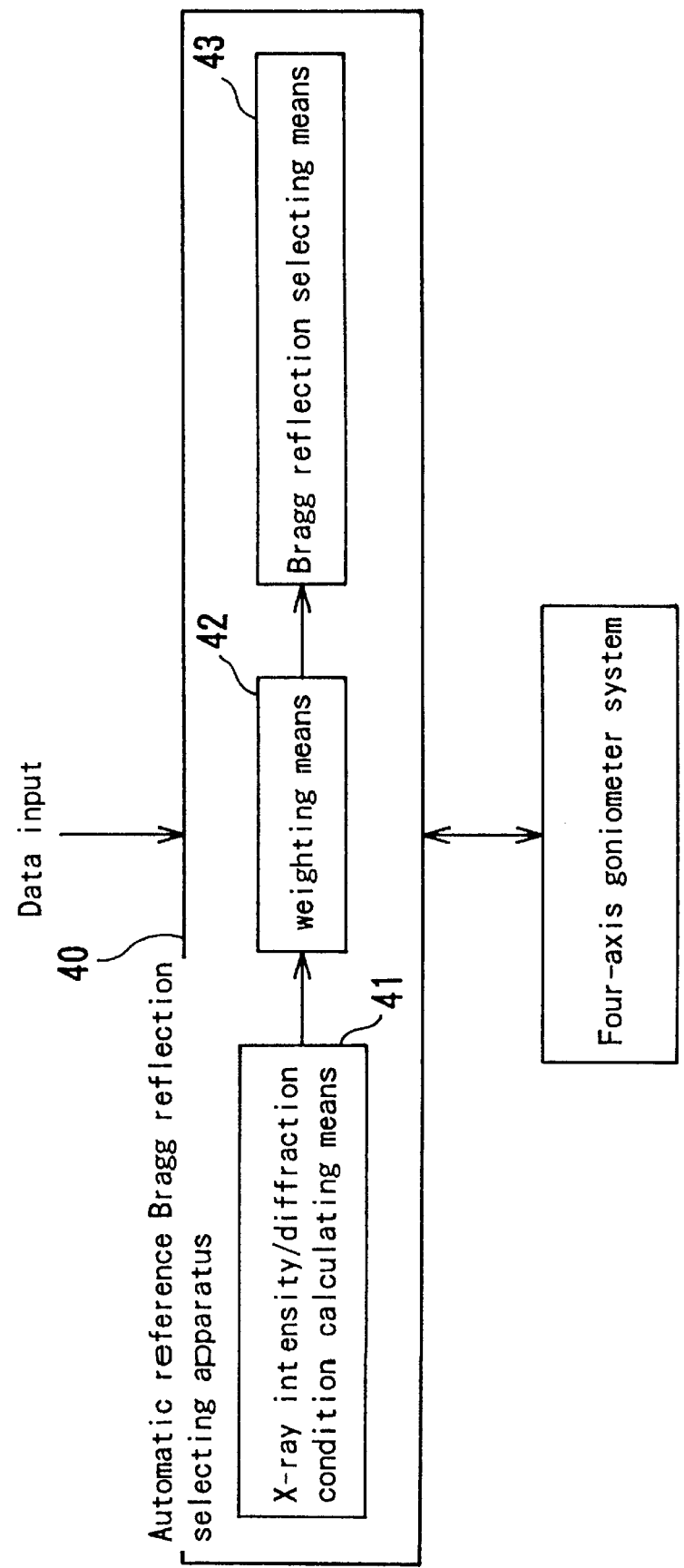
FIG. 8 is a schematic block diagram showing an example of an apparatus for automatically selecting Bragg reflections in accordance with the present invention.

FIG. 8 shows an automatic Bragg reflection selection apparatus 40 in accordance with the present invention. For example, this automatic selecting apparatus 40 is a computer system equipped with an x-ray intensity/diffraction condition calculating means 41, a weighting means 42, and a Bragg reflection selecting means 43.

The x-ray intensity/diffraction condition calculating means 41 calculates the x-ray intensities and the diffraction conditions, i.e., 2θ-angles, ω-angles, χ-angles, and φ-angles, of all measurable reference Bragg reflections using the entered crystallographic information, e.g., the space group, lattice constants, atomic positions, temperature constants, the sample normal, and the direction of incident x-rays. The calculated data are then sent to the weighting means 42. The x-ray intensities and the diffraction conditions are computed in the same way as in the method of the present invention described above in detail.

Next, the weighting means 42 assigns weight-points to the Bragg reflections depending on their x-ray intensities and on their angles ΔG. This is done with the same way as the weighting operation performed by the aforementioned Bragg reflection selecting method in accordance with the present invention. That is, first, points A are obtained by normalizing structure factors of the Bragg reflections with the structure factor of the Bragg reflection having the maximum x-ray intensity, and points B are obtained by calculating the cosines of the angles ΔG of the Bragg reflections, then each of weight-points is calculated using the equation B×m/100+B×n/100 where values of m and n represent the occupancies of A and B and are assigned to the respective Bragg reflections.

Then, the Bragg reflection selecting means 43 selects reference Bragg reflections pc1 and pc2 which are not in the line drawn by the origin and the first Bragg reflection and have the two largest weight-points in the same way as in the method of the present invention described above in detail.

Accordingly, in the automatic reference Bragg reflection selecting apparatus of the present invention, performing necessary process by the above-mentioned means, two reference Bragg reflections which together form a basis in determination of the crystallographic orientation of a crystal sample by the two-reflection method can be selected easily and automatically, thus, a series of processing steps for determination of the crystallographic orientation by the two-reflection method can be automatically done by the computer simply by entering necessary data.

Figure 9:
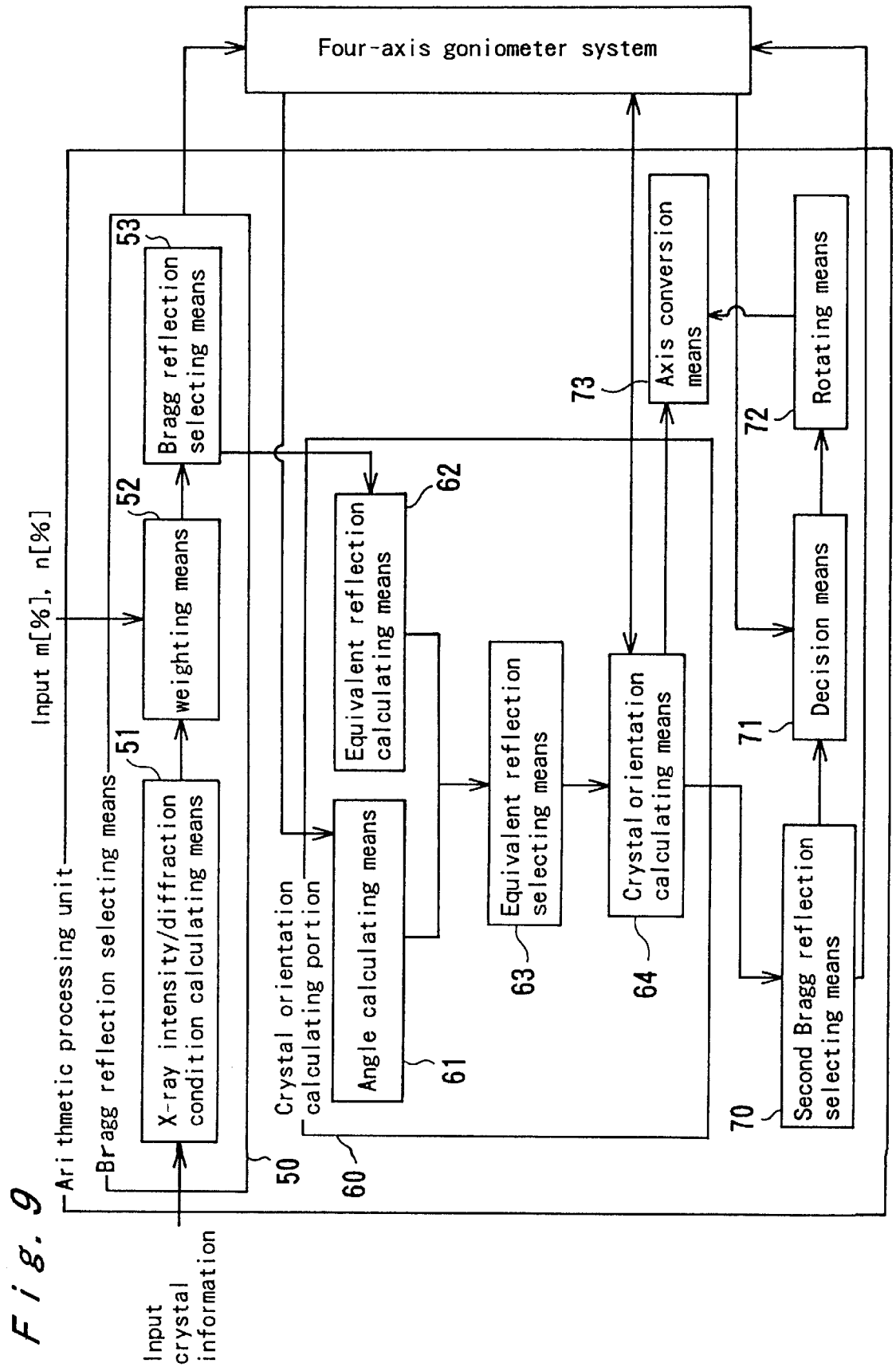
FIG. 9 is a schematic block diagram showing an example of a system for automatically determining crystallographic orientation in accordance with the present invention.

FIG. 9 shows an automatic crystallographic orientation determination system in accordance with the present invention. This determination system comprises an arithmetic processing unit that is a computer for performing various arithmetic operations and a four-axis goniometer system for performing various measurements according to the results of the calculations performed by the arithmetic processing unit. The four-axis goniometer system has a well-known construction such as the one exemplified in FIGS. 2 and 3.

The arithmetic processing unit has a Bragg reflection selecting portion 50 for selecting two Bragg reflections and a crystallographic orientation calculating portion 60 for calculating the crystallographic orientation using the values measured by the four-axis goniometer system.

The Bragg reflection selecting portion 50 comprises an x-ray intensity/diffraction condition calculating portion 51 for calculating the x-ray intensities and the diffraction conditions, i.e., 2θ-angles, ω-angles, χ-angles, and φ-angles, of all measurable reference Bragg reflections using crystallographic information given thereto, a weighting means 52 for assigning weights to the Bragg reflections according to the x-ray intensities calculated by the intensity/diffraction condition calculating portion 51 and the angles ΔG between the sample normals and scattering vectors, and a Bragg reflection selecting means 53 for selecting reference Bragg reflections pc1 and pc2 which are not on the line drawn by the origin and the first Bragg reflection and also have the two largest weight-points assigned by the weighting means 52. This Bragg reflection selecting portion 50 performs necessary processing steps as done by the aforementioned automatic Bragg reflection selecting apparatus of the present.

After selecting the reference Bragg reflections pc1 and pc2, the Bragg reflection selecting means 50 sends the diffraction condition, i.e., $2\theta_1$-angle, $\omega_1$-angle, $\chi_1$-angle, and $\phi_1$-angle, of the reference Bragg reflection pc1 and the diffraction condition, i.e., $2\theta_2$-angle, $\omega_2$-angle, $\chi_2$-angle, and $\phi_2$-angle, of the reference Bragg reflection pc2 to the four-axis goniometer system. This goniometer system searches and measures actual Bragg reflections po1 and po2 satisfying $2\theta_1$-angle, $\omega_1$-angle, $\chi_1$-angle, and $\phi_1$-angle and $2\theta_2$-angle, $\omega_2$-angle, $\chi_2$-angle, and $\phi_2$-angle, respectively. Then, these Bragg reflections po1 and po2 are sent to a crystallographic orientation calculating portion 60. This crystallographic orientation calculating portion 60 has an angle calculating means 61, an equivalent reflection calculating means 62, an equivalent reflection selecting means 63, and a crystallographic orientation calculating means 64.

In the crystallographic orientation calculating portion 60, the angle calculating means 61 calculates the angle $\alpha_0$ between the Bragg reflections po1 and po2. And, the equivalent reflection calculating means 62 finds equivalent reflections of the reference Bragg reflections pc1 and pc2, respectively, by symmetrical operations.

Subsequently, the equivalent reflection selecting means 63 selects a combination of equivalent reflections pc1' and pc2' having characteristics described below from the equivalent reflections for each of the reference Bragg reflections pc1 and pc2, respectively. The angle $\alpha_c$ between the selected equivalent reflections pc1' and pc2' is equal to the angle $\alpha_0$ between the actual Bragg reflections po1 and po2, and their scattering vector lengths are equal to those of the reference Bragg reflections pc1 and pc2, respectively. This selecting operation is carried out by a sequence of operations forming a loop until the relation where $\alpha_c = \alpha_0$ is achieved and relation where the scattering vector lengths are respectively equal to those of the reference Bragg reflections pc1 and pc2 is obtained in the same way as the aforementioned method of the present invention.

Then, with respect to the selected equivalent reflections pc1' and pc2', the crystallographic orientation calculating means 64 exchanges data with the four-axis goniometer system and calculates the crystallographic orientation by the well-known two-reflection method.

In addition, it is preferable that the automatic crystallographic orientation determination system of the present invention can cope with the case in which the crystal system of the crystal structure having a crystallographic orientation calculated by the crystallographic orientation calculating means 64 is trigonal.

This may be done by the arithmetic processing unit having a second Bragg reflection selecting means 70 for selecting a Bragg reflection p1 and a Bragg reflection p2 obtained by rotating the Bragg reflection p1 by 60° along the c-axis, wherein both p1 and p2 are not on the c-axis. When the second Bragg reflection selecting means 70 sends the diffraction conditions of the Bragg reflections p1 and p2 to the four-axis goniometer system, the four-axis goniometer system measures the x-ray intensities I1 and I2 of the Bragg reflections p1 and p2, respectively, and gives the measured values to the arithmetic processing unit.

The arithmetic processing unit is further provided with a magnitude decision means 71 and a rotating means 72. The magnitude decision means 71 makes a decision as to whether the intensity relation between the x-ray intensities I1 and I2 in magnitude agrees with the structure factor relation between the structure factors of the Bragg reflections p1 and p2 in magnitude. If the result of the decision is that both relations do not agree, the rotating means 72 rotates the crystal structure by 60° along the c-axis.

As a result of these operations, true crystal orientations of various crystal samples with known crystal structures can be automatically identified.

The arithmetic processing unit may be provided with an axis conversion means 73 for converting crystal axes to make the above-calculated crystallographic orientation as close as possible to or as same as the crystallographic orientation separately calculated using crystallographic information. The axis conversion means 73 can realize more accurate determination of crystallographic orientation.

In this way, in accordance with the automatic crystallographic orientation determination system of the present invention, necessary calculations and measurements can be automatically performed in one continuous process, thereby realizing easy and automatic determination of the crystallographic orientation of a crystal sample, thus excellent analysis of crystal structure can be realized.

Obviously, the automatic Bragg reflection selecting apparatus in accordance with the invention or the automatic crystallographic orientation determination system in accordance with the invention may be incorporated in the computer 130 of the well-known four-axis goniometer system described previously in conjunction with FIG. 3 or may be a separate computer.

EXAMPLE

The crystallographic orientation of a crystal sample $Al_2O_3$ were determined utilizing the present invention.
Crystallographic information entered first is given in Table 1 below.

TABLE 1

| sample name | $Al_2O_3$ | | | | | | |
|---|---|---|---|---|---|---|---|
| space group | 167 | | | | | | |
| lattice constants | 4.762 | 4.762 | 12.995 | 90.000 | 90.000 | 120.00 | 255.20 |
| atomic positions | Al | 0.00 | 0.00 | 0.35216 | | | |
| | 0 | 0.3061 | 0.00 | 0.25 | | | |
| temperature factors | Al | 0.31 | | | | | |
| | 0 | 0.31 | | | | | |
| sample normal direction of incident x-rays | 0 | 0 | 1 | | | | |
| | 0 | 1 | 0 | | | | |

The aforementioned various processing steps were carried out by a computer and a 4-axis goniometer using the entered crystallographic information as described above. As the crystallographic orientation, the off angle between the sample normal and a specified surface normal having 0.0866° was automatically obtained. As another crystallographic orientation, the angle between the direction of incoming x-rays and a specified incident direction having 27.9615° was also automatically obtained. Consequently, the crystal structure could be analyzed accurately.

As described above in detail, the present invention provides a novel automatic Bragg reflection selecting method and apparatus and a novel automatic crystallographic orientation determination method and system that can easily and automatically determine precise crystallographic orientations of crystal samples. The use of the present invention permits crystal samples to be structure analyzed and characterized very easily and accurately.

This invention should not be limited only to the aforementioned embodiments, and it will be understood by those skilled in the art that other changes in form and details may be made therein without departing from the spirit and scope of the invention.

What is claimed is:

1. A method of automatically selecting, using a computer, a reference Bragg reflection pc1 and a reference Bragg reflection pc2 which together form a basis for determination of the crystallographic orientation of a crystal sample by the two-reflection method, said method comprising the steps of:
    <a> calculating, using crystallographic information given to the computer, x-ray intensities and diffraction conditions of all Bragg reflections which are measurable;
    <b> assigning a weight-point to each of the Bragg reflections according to the x-ray intensity thereof and the angle ΔG between the sample normal and the scattering vector thereof; and
    <c> selecting, among the Bragg reflections, one Bragg reflection having the largest weight-point as said reference Bragg reflection pc1 and another Bragg reflection having the second largest weight-point as said reference Bragg reflection pc2.

2. The method as claimed in claim 1, wherein step <b> comprising the steps of:
    obtaining, for each of the Bragg reflections, a point A by normalizing the structure factor thereof with the structure factor of the Bragg reflection having the maximum x-ray intensity and a point B by calculating the cosine of said angle ΔG thereof;
    calculating the weight-point for the each of the Bragg reflections given by A×m/100+B×n/100 where the values of m and n represent the occupancies of the points A and the point B in the weight-point.

3. The method as claimed in claim 1, wherein at least space groups, lattice constants, and atomic positions are given to the computer as the crystallographic information.

4. The method as claimed in claim 1, wherein said diffraction conditions are calculated where any one angle among an incident angle, an outgoing reflection angle, an ω-angle, a χ-angle, and a φ-angle is in a given condition.

5. The method as claimed in claim 1, wherein at least space groups, lattice constants, and atomic positions are given to the computer as the crystallographic information, and said diffraction conditions are calculated where any one angle among an incident angle, an outgoing reflection angle, an ω-angle, a χ-angle, and a φ-angle is in a given condition.

6. A method of automatically determining the crystallographic orientation of a crystal sample using a computer for performing calculations and a four-axis goniometer system for performing measurements according to the results of calculations made by the computer, said method comprising the steps of:
    <a> calculating, using crystallographic information given to the computer, x-ray intensities and diffraction conditions of all Bragg reflections which are measurable;
    <b> assigning a weight-point to each of the Bragg reflections according to the x-ray intensity thereof and the angle ΔG between the sample normal and the scattering vector thereof;
    <c> selecting, among the Bragg reflections, one Bragg reflection having the largest weight-point as a reference Bragg reflection pc1 and another Bragg reflection having the second largest weight-point as a reference Bragg reflection pc2;
    <d> searching and measuring, by the four-axis goniometer system, an actual Bragg reflection po1 which satisfies a diffraction condition of the reference Bragg reflection pc1 and an actual Bragg reflection po2 which satisfies a diffraction condition of the reference Bragg reflection pc2;
    <e> calculating the angle $\alpha_0$ between the actual Bragg reflection po1 and the actual Bragg reflection po2;
    <f> finding equivalent reflections for each of the reference Bragg reflection pc1 and the reference Bragg reflection pc2 by symmetrical operations;
    <g> selecting a combination of an equivalent reflection pc1' and an equivalent reflection pc2' from said equivalent reflections, wherein said combination has the angle between the equivalent reflection pc1' and the equivalent reflection pc2' equal to said angle $\alpha_0$ and also has the scattering vector length for each of the equivalent reflections pc1' and the equivalent reflection pc2' coincident, respectively, with the scattering vector length for each of the reference Bragg reflection pc1 and the reference Bragg reflection pc2; and
    <h> calculating said crystallographic orientation about the equivalent reflection pc1' and the equivalent reflection pc2' by the two-reflection method.

7. The method as claimed in claim 6 further comprising the steps of:
    deciding whether the crystal system of the crystal construction having said crystallographic orientation calculated in step <h> is trigonal.

8. The method as claimed in claim 7 further comprising the steps of:
    selecting a Bragg reflection p1 which is not on the c-axis and a Bragg reflection p2 which is obtained by rotating the Bragg reflection p1 by 60° along the c-axis;
    measuring x-ray intensity I1 of the Bragg reflection p1 and x-ray intensity I2 of the Bragg reflection p2 by the four-axis goniometer system;
    deciding whether the intensity relation in magnitude between the x-ray intensity I1 and the x-ray intensity I2 agrees with the structure factor relation in magnitude between the structure factors of the Bragg reflection p1 and the Bragg reflection p2 or not; and
    rotating said crystal structure by 60° along the c-axis if said intensity relation does not agree with said structure factor relation.

9. The method as claimed in claim 8 further comprising the step of:
    performing crystal axis conversion to make the crystallographic orientation calculated in step <h> as close as possible or as same as another crystallographic orientation calculated separately using the crystallographic information if the crystal system of the crystal structure having the crystallographic orientation calculated in step <h> is trigonal.

10. The method as claimed in claim 6, wherein step <h> comprising the step of:

obtaining, for each of the Bragg reflections, a point A by normalizing the structure factor thereof with the structure factor of the Bragg reflection having the maximum x-ray intensity and a point B by calculating the cosine of said angle $\Delta G$ thereof;

calculating the weight-point for the each of the Bragg reflections given by $$A \times m/100 + B \times n/100$$

where the values of m and n represent the occupancies of the point A and the point B in the weight-point.

11. The method as claimed in claim 6, wherein at least space groups, lattice constants, and atomic positions are given to the computer as the crystallographic information.

12. The method as claimed in claim 6, wherein said diffraction conditions are calculated where any one angle among an incident angle, an outgoing reflecting angle, an $\omega$-angle, a $\chi$-angle, and a $\phi$-angle is in a given condition.

13. The method as claimed in claim 6, wherein at least space groups, lattice constants, and atomic positions are given to the computer as the crystallographic information, and said diffraction conditions are calculated where any one angle among an incident angle, an outgoing reflection angle, an $\omega$-angle, a $\chi$-angle, and a $\phi$-angle is in a given condition.

14. The method as claimed in claim 6, wherein the off angle between the sample normal and a specified surface normal is calculated as said crystallographic orientation.

15. The method as claimed in claim 6, wherein the angle between the incident x-rays and a specified incident direction is calculated as said crystallographic orientation.

16. An apparatus for automatically selecting a reference Bragg reflection pc1 and a reference Bragg reflection pc2 which together form a basis for determination of the crystallographic orientation of a crystal sample by the two-reflection method, said apparatus comprising:

an x-ray intensity/diffraction condition calculating means for calculating, using crystallographic information given thereto, x-ray intensities and diffraction conditions of all Bragg reflections which are measurable;

a weighting means for assigning a weight-point to each of the Bragg reflections according to the x-ray intensity thereof and the angle $\Delta G$ between the sample normal and the scattering vector thereof; and a Bragg reflection selecting means for selecting, among the Bragg reflections, one Bragg reflection having the largest weight-point as said reference Bragg reflection pc1 and another Bragg reflection having the second largest weight-point as said reference Bragg reflection pc2.

17. The apparatus as claimed in claim 16, wherein said weighting means performs the function of;

obtaining, for each of the Bragg reflections, a point A by normalizing the structure factor thereof with the structure factor of the Bragg reflection having the maximum x-ray intensity and a point B by calculating the cosine of said angle $\Delta G$ thereof;

calculating the weight-point for the each of the Bragg reflections given by $$A \times m/100 + B \times n/100$$

where the values of m and n represent the occupancies of the point A and the point B in the weight-point.

18. The apparatus as claimed in claim 16, wherein at least a space group, lattice constants, and atomic positions are given as the crystallographic information.

19. The apparatus of claim 16, wherein the x-ray intensity/diffraction condition calculating means calculates said diffraction conditions where any one angle among an incident angle, an outgoing reflection angle, an $\omega$-angle, a $\chi$-angle, and a $\phi$-angle is in a given condition.

20. The apparatus of claim 16, wherein at least a space group, a lattice constant, and atomic positions are given as the crystallographic information, and the x-ray intensity/diffraction condition calculating means calculates said diffraction conditions where any one angle among an incident angle, an outgoing reflection angle, an $\omega$-angle, a $\chi$-angle, and a $\phi$-angle is in a given condition.

21. A system for automatically determining the crystallographic orientation of a crystal sample, said system having an arithmetic processing unit for calculations and a four-axis goniometer system for measurements according to the results of the calculations performed by the arithmetic processing unit, said system comprising:

said arithmetic processing unit having a Bragg reflection selecting portion for selecting a reference Bragg reflection pc1 and a reference Bragg reflection pc2, and a crystallographic orientation calculating portion for calculating the crystallographic orientation of the crystal sample using values measured by the four-axis goniometer system;

said Bragg reflection selecting portion having an x-ray intensity/diffraction condition calculating means for calculating, using crystallographic information given thereto, x-ray intensities and diffraction conditions of all Bragg reflections which are measurable, a weighting means for assigning a weight-point to each of the Bragg reflections according to the x-ray intensity thereof and the angle $\Delta G$ between the sample normal and the scattering vector thereof, and a Bragg reflection selecting means for selecting, among the Bragg reflections, one Bragg reflection having the largest weight-point as said reference Bragg reflection pc1 and another Bragg reflection having the second largest weight as the reference Bragg reflections pc2;

said four-axis goniometer system performing search and measurement of an actual Bragg reflection po1 which satisfies the diffraction conditions of the reference Bragg reflection pc1 and an actual Bragg reflection po2 which satisfies the diffraction conditions of the reference Bragg reflections pc2, wherein the reference Bragg reflection pc1 and the reference Bragg reflection pc2 are given from said Bragg reflection selecting portion;

said crystallographic orientation calculating portion having an angle calculating means for calculating the angle $\alpha_0$ between the actual Bragg reflection po1 and the actual Bragg reflection po2 which are given from said four-axis goniometer system, an equivalent reflection calculating means for calculating equivalent reflections of each of the reference Bragg reflection pc1 and reference Bragg reflection pc2 by symmetrical operations, an equivalent reflection selecting means for selecting, from said equivalent reflections, a combination of an equivalent reflection pc1' and an equivalent reflection pc2' which has an angle therebetween equal to said angle $\alpha_0$ and has the scattering vector length for each of the equivalent reflection pc1' and the equivalent reflection pc2' coincident, respectively, with the scattering length for each of the reference Bragg reflection pc1 and the reference Bragg reflection pc2, and a crystallographic orientation calculating means for calculating said crystallographic orientation about the equivalent reflection pc1' and equivalent reflection pc2' by the two-reflection method.

22. The system as claimed in claim 21, wherein
said arithmetic processing unit further has a second Bragg reflection selecting means for selecting a Bragg reflection p1 which is not on the c-axis and a Bragg reflection p2 which is obtained by rotating the Bragg reflection p1 by 60° along the c-axis;
said four-axis goniometer system further performs measurement of x-ray intensity I1 of the Bragg reflection p1 and x-ray intensity I2 of the Bragg reflection p2, and
said arithmetic processing unit further has a decision means for deciding whether the intensity relation in magnitude between the x-ray intensity I1 and the x-ray intensity I2 agrees with the structure factor relation in magnitude between the structure factors of the Bragg reflection p1 and Bragg reflection p2 or not, and a rotating means for rotating said crystal structure by 60° along the c-axis if said intensity relation does not agree with said structure factor relation;
wherein said second Bragg reflection selection means, said decision means, and said rotating means operate when the crystal system of the crystal structure of the crystal sample having said crystallographic orientation calculated by said crystallographic orientation calculating portion is trigonal.

23. The system as claimed in claim 22, wherein said arithmetic processing unit is further provided with an axis conversion means for performing a crystal axis conversion to make said crystallographic orientation calculated by said crystallographic orientation calculation means as close as possible to or as same as another crystallographic orientation calculated separately using the crystallographic information if the crystal system of the crystal construction having said crystallographic orientation calculated by said crystallographic orientation calculation means is trigonal.

24. The system as claimed in claim 21, wherein said weighting means performs the functions of;
obtaining, for each of the Bragg reflections, a point A by normalizing structure factor thereof with structure factor of the Bragg reflection having the maximum x-ray intensity and a point B by calculating the cosine of said angle $\Delta G$ thereof;
calculating the weight-point for the each of the Bragg reflections given by $$A \times m/100 + B \times n/100$$

where the values of m and n represent the occupancies of the point A and the point B in the weight-point.

25. The system as claimed in claim 21, wherein at least space groups, lattice constants, and atomic positions are given as the crystallographic information.

26. The system as claimed in claim 21, wherein said diffraction conditions are calculated by the x-ray intensity/diffraction condition calculating means where any one angle among an incident angle, an outgoing reflection angle, an $\omega$-angle, a $\chi$-angle, and a $\phi$-angle is in a given condition.

27. The system as claimed in claim 21, wherein at least space groups, lattice constants, and atomic positions are given as the crystallographic information, and said diffraction conditions are calculated by the x-ray intensity/diffraction condition calculating means where any one angle among an incident angle, an outgoing reflection angle, an $\omega$-angle, a $\chi$-angle, and a $\phi$-angle is in a given condition.

28. The system as claimed in claim 21, wherein the off angle between the sample normal and a specified surface normal is calculated as said crystallographic orientation.

29. The system as claimed in claim 21, wherein the angle between the incident x-rays and a specified incident direction is calculated as said crystallographic orientation.

* * * * *